(12) United States Patent
Huh et al.

(10) Patent No.: US 9,716,232 B2
(45) Date of Patent: Jul. 25, 2017

(54) MATERIAL FOR ORGANIC LIGHT-EMITTING DEVICE, AND ORGANIC LIGHT-EMITTING DEVICE USING SAME

(75) Inventors: Jungoh Huh, Seoul (KR); Tae Yoon Park, Daejeon (KR); Jungi Jang, Daejeon (KR); Sung Kil Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 754 days.

(21) Appl. No.: 14/240,702

(22) PCT Filed: Sep. 6, 2012

(86) PCT No.: PCT/KR2012/007185
§ 371 (c)(1),
(2), (4) Date: Feb. 24, 2014

(87) PCT Pub. No.: WO2013/036045
PCT Pub. Date: Mar. 14, 2013

(65) Prior Publication Data
US 2014/0183517 A1    Jul. 3, 2014

(30) Foreign Application Priority Data
Sep. 9, 2011    (KR) .......................... 10-2011-0091943

(51) Int. Cl.
*H01L 51/00* (2006.01)
*C09K 11/06* (2006.01)
(Continued)

(52) U.S. Cl.
CPC ........ *H01L 51/0052* (2013.01); *C07D 307/91* (2013.01); *C09B 57/00* (2013.01);
(Continued)

(58) Field of Classification Search
None
See application file for complete search history.

(56) References Cited

U.S. PATENT DOCUMENTS

| | | | |
|---|---|---|---|
| 5,281,489 | A | 1/1994 | Mori et al. |
| 2003/0044518 | A1 | 3/2003 | Senoo et al. |

(Continued)

FOREIGN PATENT DOCUMENTS

| | | |
|---|---|---|
| CN | 101432272 A | 5/2009 |
| CN | 102046613 A | 5/2011 |

(Continued)

OTHER PUBLICATIONS

Journal of Materials Chemistry, Royal Society of Chemistry, GB, vol. 15, No. 31, pp. 3233-3240.
(Continued)

*Primary Examiner* — Nathan T Leong
(74) *Attorney, Agent, or Firm* — Dentons US LLP

(57) ABSTRACT

The present specification provides an organic light emitting device comprising: a first electrode, a second electrode, and organic material layers formed of one or more layers comprising a light emitting layer disposed between the first electrode and the second electrode, wherein one or more layers of the organic material layers comprise the compound of Formula 1, or a compound in which a heat-curable or photocurable functional group is introduced into this compound.

19 Claims, 3 Drawing Sheets

(51) Int. Cl.
  *C07D 307/91* (2006.01)
  *C09B 57/00* (2006.01)
  *H01L 51/50* (2006.01)

(52) U.S. Cl.
  CPC ............ *C09B 57/008* (2013.01); *C09K 11/06* (2013.01); *H01L 51/006* (2013.01); *H01L 51/0061* (2013.01); *H01L 51/0073* (2013.01); *H01L 51/0074* (2013.01); *H01L 51/50* (2013.01); *H01L 51/5012* (2013.01); *H01L 51/5056* (2013.01); *H01L 51/5064* (2013.01); *H01L 51/5072* (2013.01); *H01L 51/5088* (2013.01)

(56) References Cited

U.S. PATENT DOCUMENTS

| | | | |
|---|---|---|---|
| 2006/0142520 A1* | 6/2006 | Jones | C08F 212/14 526/328.5 |
| 2007/0224446 A1 | 9/2007 | Nakano et al. | |
| 2007/0278938 A1 | 12/2007 | Yabunouchi et al. | |
| 2009/0017331 A1 | 1/2009 | Iwakuma et al. | |
| 2010/0001636 A1 | 1/2010 | Yabunouchi | |
| 2011/0168992 A1 | 7/2011 | Bae et al. | |
| 2011/0278551 A1 | 11/2011 | Yabunouchi et al. | |
| 2011/0315965 A1 | 12/2011 | Takashima et al. | |
| 2012/0119197 A1 | 5/2012 | Nishimura et al. | |
| 2012/0146014 A1 | 6/2012 | Kato | |
| 2012/0248426 A1* | 10/2012 | Kato | C07D 209/86 257/40 |
| 2014/0027747 A1 | 1/2014 | Mun et al. | |

FOREIGN PATENT DOCUMENTS

| | | | |
|---|---|---|---|
| CN | 102482215 A | | 5/2012 |
| EP | 1 146 574 A2 | | 10/2001 |
| EP | 1892776 A2 | | 2/2008 |
| EP | 2011790 A1 | | 1/2009 |
| EP | 2166583 A1 | | 3/2010 |
| JP | 2006-151844 A | | 6/2006 |
| JP | 2014527021 A | | 10/2014 |
| KR | 10-2008-0104025 A | | 11/2008 |
| KR | 10-2011-0011647 | | 2/2011 |
| KR | 10-1029082 B1 | | 4/2011 |
| TW | 201129546 A1 | | 9/2011 |
| TW | 201213497 A1 | | 4/2012 |
| WO | 2007/125714 | † | 11/2007 |
| WO | 2007/125714 A1 | | 11/2007 |
| WO | 2009/145016 | † | 12/2009 |
| WO | 2009/145016 A1 | | 12/2009 |
| WO | 2010061824 A1 | | 6/2010 |
| WO | 2010/074087 A1 | | 7/2010 |
| WO | 2010-074087 A1 | | 7/2010 |
| WO | 2010074087 A1 | | 7/2010 |
| WO | 2011/021520 | † | 2/2011 |
| WO | 2011021520 A1 | | 2/2011 |
| WO | 2011/005099 A1 | | 5/2011 |
| WO | 2011-059099 A1 | | 5/2011 |
| WO | 2011059099 A1 | | 5/2011 |

OTHER PUBLICATIONS

Huang, Tai-Hsiang, et al., "Organic electroluminescent derivatives containing dibenzothiophene and diarylamine segments", Journal of Materials Chemistry, 2002, 15, p. 3233-3240.

\* cited by examiner
† cited by third party

[Figure 1]
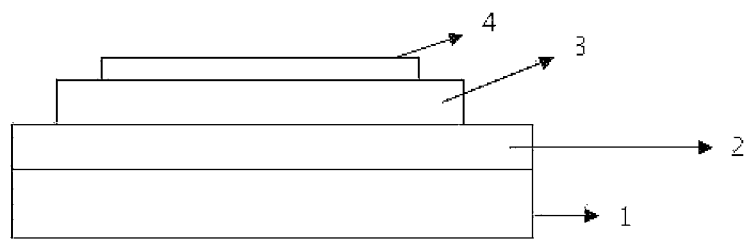

[Figure 2]
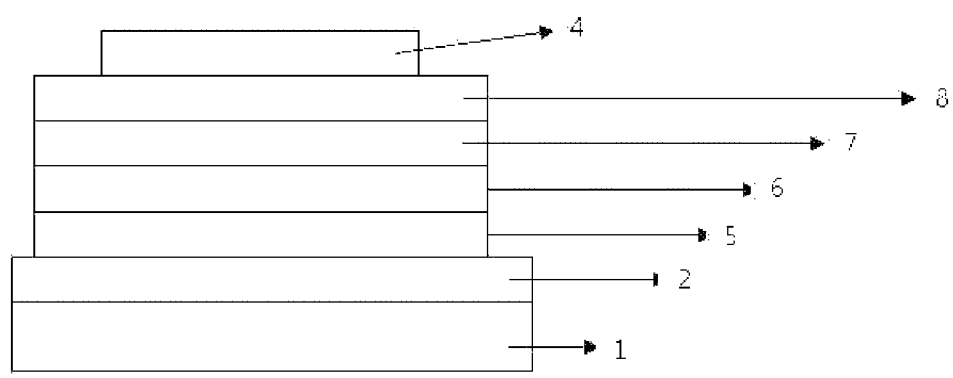

[Figure 3]
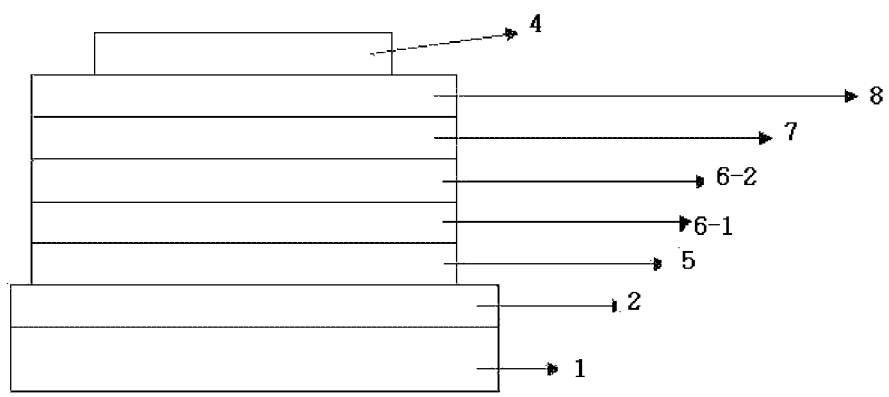

MATERIAL FOR ORGANIC LIGHT-EMITTING DEVICE, AND ORGANIC LIGHT-EMITTING DEVICE USING SAME

This application is a National Stage Application of International Patent Application No. PCT/KR2012/007185, filed on Sep. 6, 2012, which claims priority to and the benefit of Korean Patent Application No. 10-2011-0091943, filed on Sep. 9, 2011 in the Korean Intellectual Property Office, all of which are hereby incorporated by reference.

TECHNICAL FIELD

The present specification relates to a dibenzothiophene-based compound that is capable of largely improving life span, efficiency, electrochemical stability, and thermal stability of an organic light emitting device, and an organic light emitting device in which the dibenzothiophene-based compound is comprised in an organic compound layer.

BACKGROUND ART

An organic light emitting phenomenon is an example of a conversion of current into visible rays by an internal process of a specific organic molecule. The organic light emitting phenomenon is based on the following principle. When an organic material layer is positioned between an anode and a cathode, if voltage is applied between two electrodes, electrons and holes are injected from the cathode and the anode to the organic material layer, respectively. The electrons and the holes injected into the organic material layer are recombined to form an exciton, and the exciton falls down to a bottom state to emit light. In general, an organic light emitting device using this principle may be constituted by a cathode, an anode, and an organic material layer interposed therebetween, for example, an organic material layer comprising a hole injection layer, a hole transport layer, a light emitting layer, and an electron transport layer.

The materials used in the organic light emitting device are mostly pure organic materials or complexes of the organic material and metal, and may be classified into a hole injection material, a hole transport material, a light emitting material, an electron transport material, an electron injection material, and the like according to the purpose thereof. In this case, an organic material having a p-type property, that is, an organic material that is easily oxidized and is electrochemically stable during oxidation, is mainly used as the hole injection material or the hole transport material. Meanwhile, an organic material having an n-type property, that is, an organic material that is easily reduced and is electrochemically stable during reduction, is mainly used as the electron injection material or the electron transport material. A material having both p-type and n-type properties, that is, a material that is stable when the material is oxidized and reduced, is preferable as the light emitting layer material, and a material having high light emitting efficiency for conversion of the exciton into light when the exciton is formed is preferable.

In addition, it is preferable that the material used in the organic light emitting device further have the following properties.

First, it is preferable that the material used in the organic light emitting device have excellent thermal stability. This is because joule heat is generated by movement of electric charges in the organic light emitting device. Recently, since NPB, which has been mainly used as the hole transport layer material, has a glass transition temperature of 100° C. or lower, there is a problem in that it is difficult to use NPB in an organic light emitting device requiring a high current.

Second, holes or electrons injected into the organic light emitting device should be smoothly transported to a light emitting layer, and the injected holes and electrons should not be released out of the light emitting layer in order to obtain an organic light emitting device that is capable of being driven at low voltage and has high efficiency. To this end, a material used in the organic light emitting device should have an appropriate band gap and HOMO or LUMO energy level. Since a LUMO energy level of PEDOT:PSS, which is currently used as the hole transport material in the organic light emitting device manufactured by a solution coating method, is lower than that of an organic material used as the light emitting layer material, it is difficult to manufacture an organic light emitting device having high efficiency and a long life span.

In addition, the material used in the organic light emitting device should have excellent chemical stability, electric charge mobility, and interfacial characteristic with an electrode or an adjacent layer. That is, the material used in the organic light emitting device should be less deformed by moisture or oxygen.

Further, appropriate hole or electron mobility should be ensured so as to balance densities of the holes and of the electrons in the light emitting layer of the organic light emitting device, thus maximizing formation of excitons. In addition, an interface with an electrode comprising metal or metal oxides should be favorable for stability of the device.

Accordingly, there is a need to develop an organic material having the aforementioned requirements in the art.

PRIOR ART DOCUMENT

Patent Document

U.S. Application Laid-Open No. 2003-0044518
European Patent Application Laid-Open No. 1146574 A2

DISCLOSURE

Technical Problem

The present inventors aim to provide a heterocompound derivative that can satisfy conditions required in a material used in an organic light emitting device, for example, an appropriate energy level, electrochemical stability, thermal stability, and the like, and has a chemical structure that can perform various roles required in the organic light emitting device according to a substituent group, and an organic light emitting device including the same.

Technical Solution

An exemplary embodiment of the present specification provides a dibenzothiophene-based compound represented by the following Formula 1:

[Formula 1]

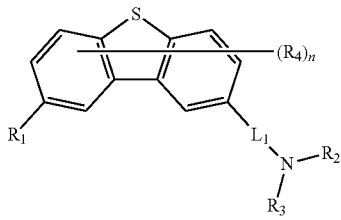

wherein, $L_1$ is an arylene group having 6 to 40 carbon atoms; or a fluorenylene group substituted by an alkyl group, $R_1$ is hydrogen; an alkyl group having 1 to 20 carbon atoms; an alkoxy group having 1 to 20 carbon atoms; or an aryl group having 6 to 12 carbon atoms substituted or unsubstituted by an alkyl group having 1 to 20 carbon atoms or an alkoxy group having 1 to 20 carbon atoms, $R_2$ and $R_3$ are different from each other, $R_2$ is a phenyl group substituted or unsubstituted by one or more substituted groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; or a biphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group, $R_3$ is a terphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; a tetraphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; or a naphthyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group, $R_4$ is hydrogen; an alkyl group having 1 to 20 carbon atoms, or an alkoxy group having 1 to 20 carbon atoms, and may form an aliphatic, aromatic, or hetero condensated cycle with an adjacent group, and n means the number of substituent groups, and is an integer of 1 to 6.

Another exemplary embodiment of the present specification provides an organic light emitting device comprising: a first electrode, a second electrode, and organic material layers formed of one or more layers comprising a light emitting layer disposed between the first electrode and the second electrode, wherein one or more layers of the organic material layers comprise the dibenzothiophene-based compound of Formula 1, or a compound in which a heat-curable or photocurable functional group is introduced into the dibenzothiophene-based compound.

Advantageous Effects

A compound of the present specification may be used as an organic material layer material, particularly, a hole injection material and/or a hole transport material in an organic light emitting device, and in the case where the compound is used in the organic light emitting device, a driving voltage of the device is lowered, light efficiency is improved, and a life span property of the device is improved because of thermal stability of the compound.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting diode comprising a substrate 1, an anode 2, a hole injection layer 5, a hole transport layer 6, a light emitting layer 7, an electron transport layer 8, and a cathode 4.

FIG. 3 shows an example of an organic light emitting device in which a substrate 1, an anode 2, a hole injection layer 5, a hole transport layer 6-1 not comprising a compound represented by Formula 1, a hole transport layer 6-2 comprising the compound represented by Formula 1, a light emitting layer 7, an electron transport layer 8, and a cathode 4 are sequentially laminated.

BEST MODE

The present specification provides a dibenzothiophene-based compound represented by the following Formula 1.

Further, the present specification provides an organic light emitting device comprising: a first electrode, a second electrode, and organic material layers formed of one or more layers comprising a light emitting layer disposed between the first electrode and the second electrode, wherein one or more layers of the organic material layers comprise the dibenzothiophene-based compound of Formula 1, or a compound in which a heat-curable or photocurable functional group is introduced into the dibenzothiophene-based compound.

Examples of the substituent groups will be described below, but are not limited thereto.

In the present specification, the alkyl group may be a straight chain or a branched chain, and has 1 to 20 carbon atoms. Specific examples thereof comprise a methyl group, an ethyl group, a propyl group, an isopropyl group, a butyl group, a t-butyl group, a pentyl group, a hexyl group, a heptyl group, and the like, but are not limited thereto.

In the present specification, the alkenyl group may be a straight chain or a branched chain, and has 2 to 20 carbon atoms. Specific examples thereof preferably comprise an alkenyl group in which an aryl group such as a stylbenzyl group and a styrenyl group is substituted, but are not limited thereto.

In the present specification, the alkoxy group may be a straight chain or a branched chain, and has 1 to 20 carbon atoms.

In the present specification, an aryl group of $R_1$ of Formula 1 may be a monocycle type or a polycycle type, and has 6 to 12 carbon atoms. Specific examples of the aryl group comprise monocyclic aromatics such as a phenyl group, a biphenyl group, and a triphenyl group, and polycyclic aromatics such as a naphthyl group, but are not limited thereto.

In the present specification, an arylene group and a fluorenylene group of $L_1$ of Formula 1 are divalent groups of an aryl group and a fluorenyl group, respectively.

In the present specification, the aryl group of the arylene group of $L_1$ may be a monocycle type or a polycycle type, and the number of carbon atoms thereof is not particularly limited but is preferably 6 to 60. Specific examples of the aryl group comprise monocyclic aromatics such as a phenyl group, a biphenyl group, a triphenyl group, a terphenyl group, and a stilbene group, polycyclic aromatics such as a naphthyl group, a binaphthyl group, an anthracenyl group, a phenanthrenyl group, a pyrenyl group, a perylenyl group, a tetracenyl group, a crycenyl group, a fluorenyl group, an acenaphthacenyl group, a trihenylene group, and a fluoranthene group, and the like, but are not limited thereto.

In the present specification, the fluorenyl group has a structure where two cyclic organic compounds are connected through one atom, and examples thereof comprise

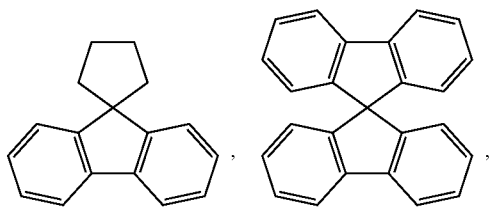

and the like.

In the present specification, the fluorenyl group comprises a structure of an opened fluorenyl group, the opened fluorenyl group has a structure where two cyclic compounds are connected through one atom and connection of one cyclic compound is broken, and examples thereof comprise

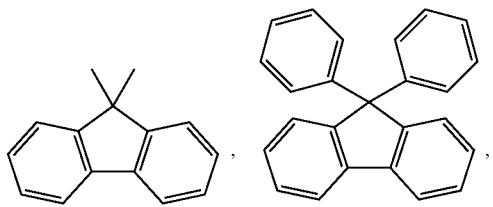

and the like.

In the exemplary embodiment of the present specification, $L_1$ is an arylene group or a fluorenylene group substituted by an alkyl group.

In the exemplary embodiment, $L_1$ is a phenylene group, a biphenylene group, or a fluorenylene group substituted by an alkyl group.

In another exemplary embodiment, $L_1$ is a phenylene group.

In another exemplary embodiment, $L_1$ is a biphenylene group.

In another exemplary embodiment, $L_1$ is a fluorenylene group substituted by a methyl group.

In another exemplary embodiment, $R_1$ is hydrogen; an alkyl group having 1 to 20 carbon atoms; an alkoxy group having 1 to 20 carbon atoms; or an aryl group substituted or unsubstituted by an alkyl group having 1 to 20 carbon atoms or an alkoxy group having 1 to 20 carbon atoms.

In the exemplary embodiment, $R_1$ is hydrogen, or a phenyl group substituted or unsubstituted by an alkyl group having 1 to 20 carbon atoms.

In another exemplary embodiment, $R_1$ is hydrogen.

In another exemplary embodiment, $R_1$ is a phenyl group or a biphenyl group.

In another example, $R_1$ is a phenyl group substituted by an alkyl group, or a biphenyl group substituted by an alkyl group.

In another example, $R_1$ is a phenyl group substituted by a methyl group, or a biphenyl group substituted by a methyl group.

In another example, $R_1$ is a phenyl group.

In the exemplary embodiment of the present specification, $R_1$ is an aryl group substituted or unsubstituted by an alkyl group having 1 to 20 carbon atoms or an alkoxy group having 1 to 20 carbon atoms. In the case where $R_1$ is the aryl group substituted by the arylamine group, a total planar surface property of the compound is excessively reduced to make crystallization easy, accordingly, it is difficult to form a stable amorphous layer, and an electron donating effect of dibenzothiophene to the connected amine group is reduced by half due to the added amine group. Therefore, it is difficult to expect to efficiently inject and/or transport holes to the light emitting layer.

In another exemplary embodiment, $R_4$ is hydrogen.

In another exemplary embodiment, $R_2$ and $R_3$ are different from each other.

In another exemplary embodiment, $R_2$ is a phenyl group substituted or unsubstituted by one or more substituted groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; or a biphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group.

In the exemplary embodiment, $R_2$ is a biphenyl group.

In another exemplary embodiment, $R_2$ is a phenyl group.

In another exemplary embodiment, $R_3$ is a terphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; a tetraphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; or a naphthyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group.

In another exemplary embodiment, $R_3$ is a terphenyl group.

In another exemplary embodiment, $R_3$ is a tetraphenyl group.

In another exemplary embodiment, $R_2$ and $R_3$ are different from each other, $R_2$ is a phenyl group, and $R_3$ is a terphenyl group.

In another exemplary embodiment, $R_2$ and $R_3$ are different from each other, $R_2$ is a biphenyl group, and $R_3$ is a terphenyl group.

In another exemplary embodiment, $R_2$ and $R_3$ are different from each other, $R_2$ is a phenyl group, and $R_3$ is a tetraphenyl group.

In another exemplary embodiment, $R_2$ and $R_3$ are different from each other, $R_2$ is a biphenyl group, and $R_3$ is a tetraphenyl group.

In another exemplary embodiment, $L_1$ is a phenylene group, a biphenylene group, or a fluorenylene group substituted by an alkyl group, $R_1$ is hydrogen, or a phenyl group substituted or unsubstituted by an alkyl group having 1 to 20 carbon atoms, $R_2$ and $R_3$ are different from each other, $R_2$ is a phenyl group or a biphenyl group, and $R_3$ is a terphenyl group or a tetraphenyl group.

In the dibenzothiophene-based compound, Formula 1 is any one of the following Formulas 1-1 to 1-8.

[Formula 1-1]

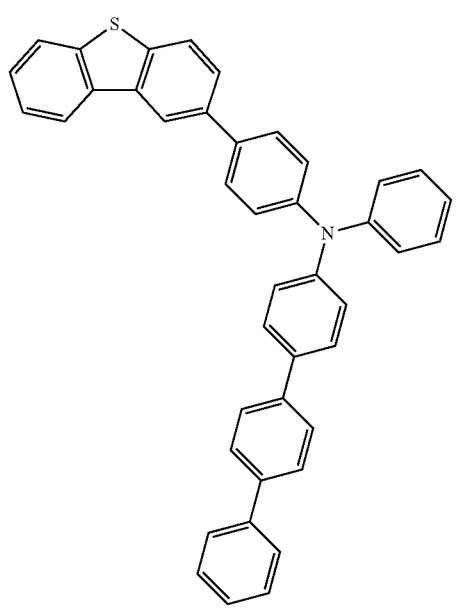

[Formula 1-2]

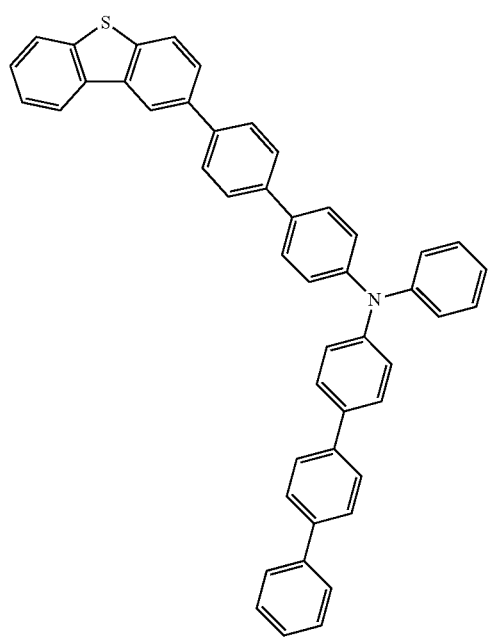

[Formula 1-3]

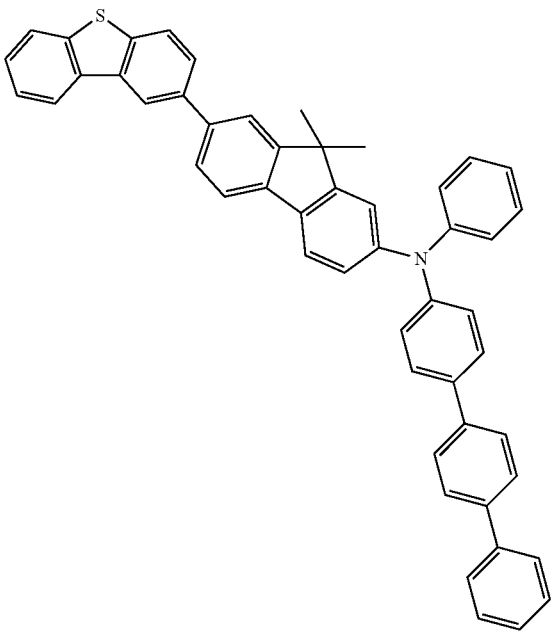

[Formula 1-4]

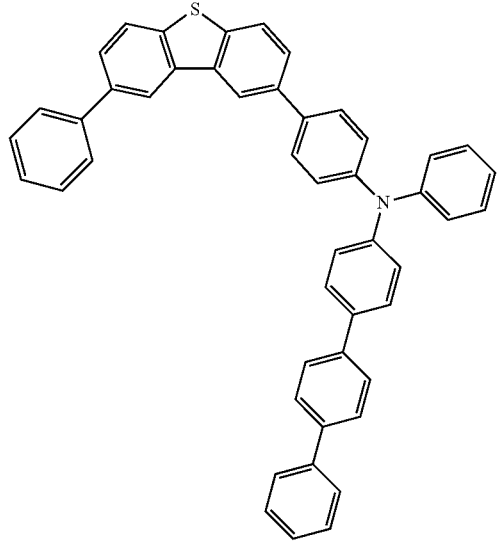

[Formula 1-5]

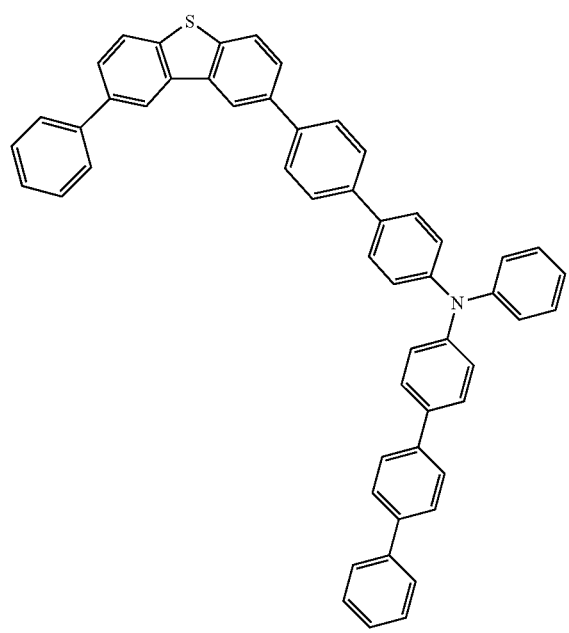

[Formula 1-6]

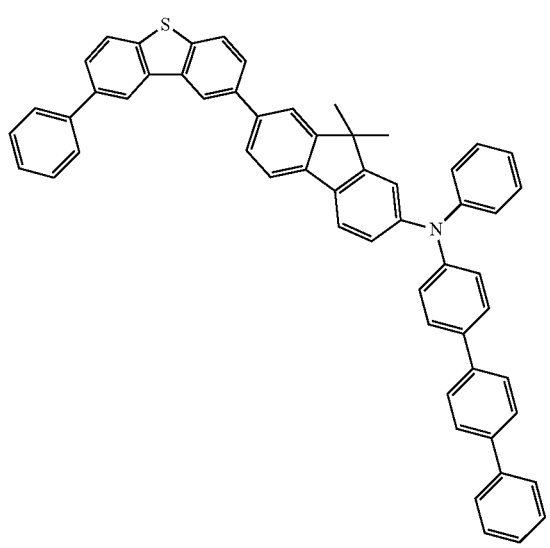

[Formula 1-7]

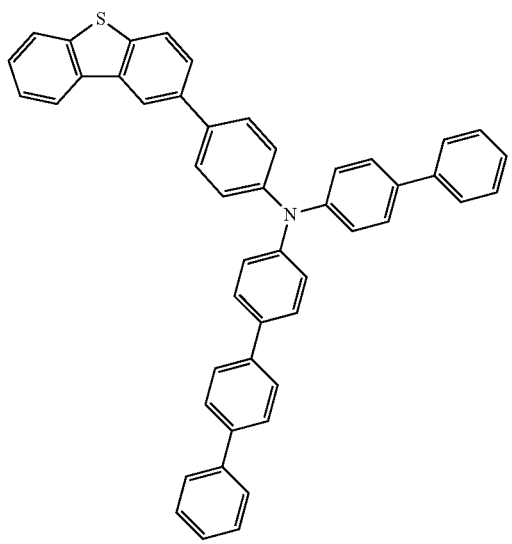

[Formula 1-8]

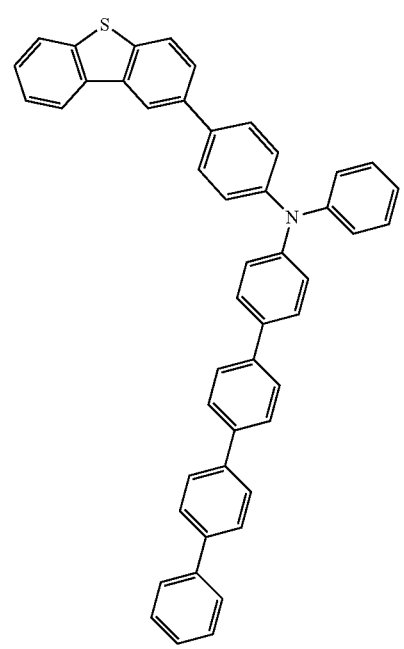

Hereinafter, the present specification will be described in detail.

The dibenzothiophene-based compound of Formula 1 generates an intermediate by substituting $L_1$ on substituted or unsubstituted dibenzothiophene. Thereafter, the compound is manufactured by a method of substituting —$NR_2R_3$ on the intermediate.

The conjugation length of the compound has a close relationship with an energy band gap. Specifically, the energy band gap is reduced as the conjugation length of the compound increases. As described above, since the core of the compound of Formula 1 comprises a limited conjugation, the core has a large energy band gap.

In the present specification, as described above, the compound having various energy band gaps may be synthesized by introducing various substituent groups at positions of $R_1$ to $R_4$ of the core structure having the large energy band gap.

Generally, it is easy to control the energy band gap by introducing substituent groups into the core structure having the large energy band gap, but it is difficult to significantly control the energy band gap by introducing substituent groups into the core structure having the small energy band gap. Further, in the present specification, it is possible to control HOMO and LUMO energy levels of the compound by introducing various substituent groups to positions of $R_1$ to $R_4$ of the aforementioned core structure.

In addition, compounds having intrinsic characteristics of the introduced substituent groups may be synthesized by introducing various substituent groups to the aforementioned core structure. For example, it is possible to synthesize a material satisfying conditions required in each organic material layer by introducing the substituent group used in a hole injection layer material, a hole transport layer material, a light emitting layer material, and an electron transport layer material used to manufacture the organic light emitting device to the core structure.

Since the compound of Formula 1 comprises an amine structure connected to the core structure by the arylene group, the compound may have an appropriate energy level as the hole injection and/or hole transport material in the organic light emitting device. In the present specification, it is possible to implement a device having low driving voltage and high light efficiency by selecting the compound having an appropriate energy level according to the substituent group among the compounds of Formula 1 and using the compound in the organic light emitting device.

In addition, the energy band gap may be finely controlled, a property at an interface between organic materials may be improved, and the purpose of the material may become various by introducing various substituent groups to the core structure.

In addition, HOMO and LUMO energy levels and the energy band gap may be finely controlled, the property at the interface between organic materials may be improved, and the purpose of the material may become various.

Meanwhile, since the compound of Formula 1 has a high glass transition temperature (Tg), thermal stability is excellent. Such increase in thermal stability is an important factor providing driving stability and a device having a long life span to the device.

Further, in Formula 1, in the case where $L_1$ is connected to the 11$^{th}$ position of dibenzothiophene in the following structure of dibenzothiophene, the electron donating effect to the connected amine group is higher than that in the case where $L_1$ is connected to the 13$^{th}$ position that is close to the sulfur element of dibenzothiophene, such that hole injection and transporting efficiencies into the light emitting layer may be increased, thus ensuring better properties in views of the voltage and efficiency.

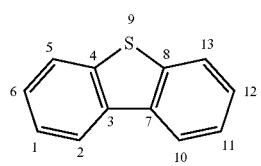

Further, in Formula 1, if $R_2$ and $R_3$ are different from each other, asymmetry of molecules is maximized as compared to the case where $R_2$ and $R_3$ are the same as each other, thus increasing polarity. Since an increase in polarity of the molecules increases the hole injection efficiency to the light emitting layer regardless of the HOMO level, it is possible to manufacture a low voltage device. An increase in polarity is confirmed from calculation of electronegativity of the molecule.

Further, the exemplary embodiment of the present specification provides an organic light emitting device comprising a first electrode, a second electrode, and organic material layers formed of one or more layers comprising a light emitting layer disposed between the first electrode and the second electrode, wherein one or more layers of the organic material layers comprise the compound of Formula 1, or a compound in which a heat-curable or photocurable functional group is introduced into the compound.

The compound according to the present specification may be used as a hole injection material, a hole transport material, a light emitting material, an electron transport material, an electron injection material, and the like, and it is more preferable that the compound be used as the hole transport material in the organic light emitting device according to the present specification.

The organic material layer of the organic light emitting device of the present specification may have a single layer structure, or a multilayered structure in which two or more organic material layers are laminated. For example, the organic light emitting device of the present specification may have a structure comprising a hole injection layer, a hole transport layer, a light emitting layer, an electron transport layer, an electron injection layer, and the like as the organic material layer. However, the structure of the organic light emitting device is not limited thereto, but may comprise a smaller number of organic material layers.

In the exemplary embodiment of the organic light emitting device of the present specification, the organic light emitting device may have the structure shown in FIGS. 1 and 2, but is not limited thereto.

FIG. 1 illustrates a structure of an organic light emitting device where on a substrate 1, an anode 2, a light emitting layer 3, and a cathode 4 are sequentially laminated. In the aforementioned structure, the compound may be comprised in the light emitting layer 3.

FIG. 2 illustrates a structure of an organic light emitting device where a substrate 1, an anode 2, a hole injection layer 5, a hole transport layer 6, a light emitting layer 7, an electron transport layer 8, and a cathode 4 are sequentially laminated. In the aforementioned structure, the compound may be comprised in one or more layers of the hole injection layer 5, the hole transport layer 6, the light emitting layer 7, and the electron transport layer 8.

The exemplary embodiment of the present specification provides the organic light emitting device where the organic material layer comprises the hole transport layer, and the hole transport layer comprises the dibenzothiophene-based compound, or the compound in which the heat-curable or photocurable functional group is introduced into the dibenzothiophene-based compound.

The exemplary embodiment of the present specification provides the organic light emitting device where the organic material layers comprise two-layered hole transport layer, and at least one or more layers of the hole transport layers comprise the compound represented by Formula 1, or the compound in which the heat-curable or photocurable functional group is introduced into the compound represented by Formula 1.

In another exemplary embodiment, the organic material layers comprise a first hole transport layer and a second hole transport layer, the first hole transport layer comprises the dibenzothiophene-based compound, or the compound in which the heat-curable or photocurable functional group is introduced into the dibenzothiophene-based compound, and the second hole transport layer adopts an aromatic amine compound. Monoamine, diamine, triamine, and tetramine are used as the aromatic amine compound. Specific examples of the aromatic amine compound comprise 4,4'-bis[N-(1-naphthyl)-N-phenyl-amino]-biphenyl (α-NPD), 4,4'-bis[N-(3-methylphenyl)-N-phenyl-amino]-biphenyl (TPD), 4,4',4"-tris(N,N-diphenyl-amino)-triphenylamine (TDATA), 4,4',4"-tris[N-(3-methylphenyl)-N-phenyl-amino]-triphenylamine (MTDATA), and the like, but are not limited thereto.

In the present specification, in the case where in the organic light emitting device comprising two or more hole transport layers, the light emitting layer is formed by using the host material having the wide energy gap, a difference between an ionization potential (IP) of the host material and an ionization potential (IP) of the hole injection and hole transport layer is increased, such that it is difficult to inject and transport holes to the light emitting layer, thus increasing the driving voltage for obtaining sufficient brightness. In this case, the holes may be easily transported to the light emitting layer by introducing a hole transport assisting layer adjacent to the light emitting layer, that is, the first hole transport layer, by using the compound of Formula 1, thus reducing the driving voltage. Further, since the first hole transport layer comprising the compound of Formula 1 may be designed to have LUMO and triplet energy values that are higher than those of the host material, the first hole transport layer prevents electrons and excitons from being provided from the light emitting layer to improve device efficiency and life span properties.

Another exemplary embodiment provides the organic light emitting device where the second hole transport layer is interposed between the anode and the first hole transport layer.

Another exemplary embodiment provides the organic light emitting device where the first hole transport layer is interposed between the light emitting layer and the second hole transport layer.

Another exemplary embodiment provides the organic light emitting device where the first hole transport layer is in contact with the light emitting layer.

In the case where the first hole transport layer comprising the dibenzothiophene-based compound represented by Formula 1 or the compound in which the heat-curable or photocurable functional group is introduced into the dibenzothiophene-based compound is in contact with the light emitting layer, the holes provided from the first electrode efficiently move to the light emitting layer, and if the ratio of the dibenzothiophene-based compound in the hole transport layer is controlled, a probability of exciton generation in the light emitting layer may be increased and the excitons may be controlled so that the excitons are generated to be uniformly spread over the entire light emitting layer. In this case, the excitons do not contribute to light emission and are provided to the adjacent electron transport layer to reduce a probability of extinction of light emission, thus improving light emission efficiency, and an effect of accelerating aging of a predetermined portion in the light emitting layer because of biasing of the excitons to one side may be prevented to implement an organic light emitting device having an improved life span.

FIG. 3 illustrates a structure of an organic light emitting device in which a substrate 1, an anode 2, a hole injection layer 5, a hole transport layer 6-1 not comprising a compound represented by Formula 1, a hole transport layer 6-2 comprising the compound represented by Formula 1, a light emitting layer 7, an electron transport layer 8, and a cathode 4 are sequentially laminated.

Another exemplary embodiment provides the organic light emitting device where the organic material layers comprise a hole injection layer, and the hole injection layer comprises the compound or the compound in which the heat-curable or photocurable functional group is introduced into the compound.

Another exemplary embodiment provides the organic light emitting device where the organic material layers comprise a layer simultaneously injecting and transporting holes, and the layer comprises the compound or the compound in which the heat-curable or photocurable functional group is introduced into the compound.

Another exemplary embodiment provides the organic light emitting device where the organic material layers comprise an electron injection and electron transport layer, and the electron injection or electron transport layer comprises the compound, or the compound in which the heat-curable or photocurable functional group is introduced into the compound.

Another exemplary embodiment provides the organic light emitting device where the organic material layers comprise a light emitting layer, and the light emitting layer comprises the compound or the compound in which the heat-curable or photocurable functional group is introduced into the compound.

Further, the compound of Formula 1 may be formed as the organic material layer by a vacuum deposition method and a solution coating method when the organic light emitting device is manufactured. Herein, the solution coating method means spin coating, dip coating, inkjet printing, screen printing, a spray method, roll coating, and the like, but is not limited thereto.

In the organic light emitting device of the present specification, the compound in which the heat-curable or photocurable functional group is introduced into the compound of Formula 1 may be used instead of the compound of Formula 1. The compound may be formed as the organic material layer by a method of forming a thin film by the solution coating method when the device is manufactured and then curing the thin film while maintaining basic physical properties of the compound of Formula 1.

As described above, the method of forming the organic material layer by introducing the curable functional group to the organic material, forming the thin film of the organic material by the solution coating method, and curing the thin film when the organic light emitting device is manufactured is described in U.S. Patent Application Laid-Open No. 2003-0044518, European Patent Application Laid-Open No. 1146574 A2, and the like.

The aforementioned documents describe that in the case where the organic light emitting device is manufactured by forming the organic material layer by the aforementioned method using the material having the heat-curable or photocurable vinyl group or acryl group, the organic light emitting device having the multilayered structure can be manufactured by the solution coating method and the organic light emitting device having the low voltage and high brightness can be manufactured. The aforementioned operation principle may be applied to even the compound of the present specification.

In the present specification, the heat-curable or photocurable functional group may be a vinyl group, an acryl group, or the like.

The organic light emitting device of the present specification may be manufactured by a material and a method known in the art, except that one or more layers of organic material layers comprise the compound of the present specification, that is, the compound of Formula 1.

For example, the organic light emitting device of the present specification may be manufactured by sequentially laminating a first electrode, an organic material layer, and a second electrode on a substrate. In this case, the organic light emitting device may be manufactured by forming an anode by depositing metal or metal oxides having the conductivity or an alloy thereof on a substrate by using a PVD (physical vapor deposition) method such as sputtering method or e-beam evaporation, forming the organic material layer comprising the hole injection layer, the hole transport layer, the light emitting layer, and the electron transport layer thereon, and then depositing the material that is capable of being used as the cathode thereon. In addition to this method, the organic light emitting device may be manufactured by sequentially depositing a cathode material, an organic material layer, and an anode material on the substrate.

Further, the compound of Formula 1 may be formed as the organic material layer by a vacuum deposition method and a solution coating method when the organic light emitting device is manufactured. Herein, the solution coating method means spin coating, dip coating, doctor blading, inkjet printing, screen printing, a spray method, roll coating, or the like, but is not limited thereto.

In the exemplary embodiment of the present specification, the first electrode may be an anode, and the second electrode may be a cathode.

In another exemplary embodiment, the first electrode may be the cathode, and the second electrode may be the anode.

It is preferable that the anode material be, in general, a material having a large work function so as to smoothly perform hole injection into the organic material layer. Specific examples of the anode material that is capable of being used in the present specification comprise metal such as vanadium, chrome, copper, zinc, and gold, or an alloy thereof; metal oxides such as zinc oxides, indium oxides, indium tin oxides (ITO), and indium zinc oxides (IZO); a combination of metal and oxides, such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

It is preferable that the cathode material be, in general, a material having a small work function so as to smoothly perform electron injection into the organic material layer. Specific examples of the cathode material comprise metal such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like but are not limited thereto.

The hole injection material is a material that is capable of well receiving holes from the anode at a low voltage, and it is preferable that the HOMO (highest occupied molecular orbital) of the hole injection material be a value between the work function of the anode material and the HOMO of the organic material layer therearound. Specific examples of the hole injection material comprise metal porphyrine, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport material is a material that is capable of receiving the holes from the anode or the hole injection layer and transporting the holes to the light emitting layer, and is preferably a material having large mobility to the holes. Specific examples thereof comprise an arylamine-based organic material, a conductive polymer, a block copolymer in which a conjugate portion and a non-conjugate portion are present together, and the like, but are not limited thereto.

The light emitting material is a material that is capable of receiving the holes and the electrons from the hole transport layer and the electron transport layer and combines the holes and the electrons to emit light in a visible ray region, and is preferably a material having excellent photon efficiency to fluorescence or phosphorescence. Specific examples thereof comprise a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The electron transport material is a material that is capable of receiving the electrons well from the cathode and transporting the electrons to the light emitting layer, and is preferably a material having large mobility to the electrons. Specific examples thereof comprise a 8-hydroxyquinoline Al complex; a complex comprising $Alq_3$; an organic radical compound; a hydroxyflavone metal complex, and the like, but are not limited thereto.

The organic light emitting device according to the present specification may be a top emission type, a bottom emission type, or a both-sided emission type according to the used material.

The compound according to the present specification may be applied to an organic electronic device such as an organic solar cell, an organic photoconductor, and an organic transistor by the principle that is similar to the principle applied to the organic light emitting device.

MODE FOR INVENTION

The method of synthesizing the organic compound represented by Formula 1 and the manufacturing of the organic light emitting device using the same will be described in more detail by the following Examples and Comparative Examples. However, the Examples are set to illustrate but are not to be construed to limit the present specification.

EXAMPLE

<Synthesis Example 1> Manufacturing of the Compound Represented by Formula 1-1

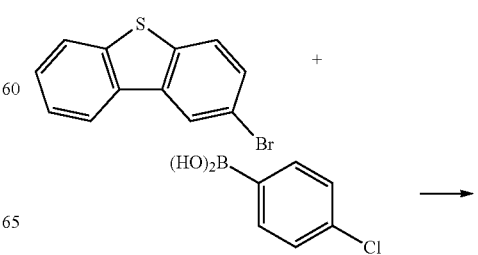

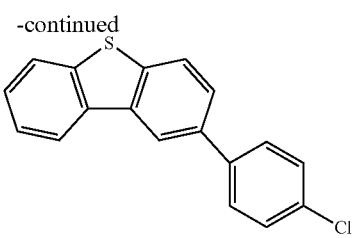

[Formula 1A]

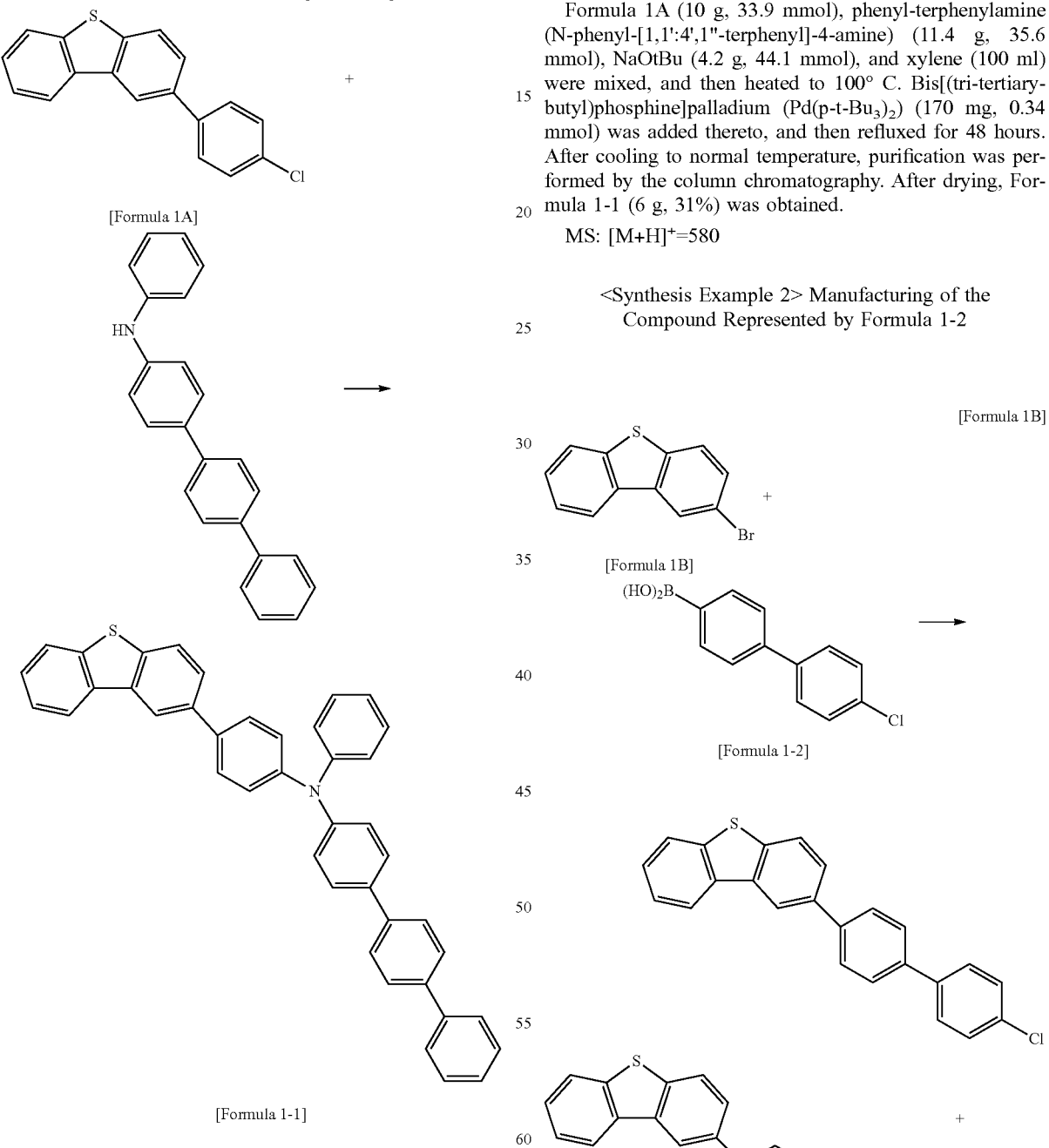

(Pd(PPh$_3$)$_4$) (1.3 g, 1.14 mmol) was added thereto, and then refluxed for 12 hours. After cooling to normal temperature, the water layer was removed. After magnesium sulfate (MgSO$_4$) was added to the organic layer, filtration was performed. After concentration, purification was performed by the column chromatography to obtain Formula 1A (20 g, yield 60%).

MS: [M+H]$^+$=294

(3) Manufacturing of Formula 1-1

Formula 1A (10 g, 33.9 mmol), phenyl-terphenylamine (N-phenyl-[1,1':4',1''-terphenyl]-4-amine) (11.4 g, 35.6 mmol), NaOtBu (4.2 g, 44.1 mmol), and xylene (100 ml) were mixed, and then heated to 100° C. Bis[(tri-tertiary-butyl)phosphine]palladium (Pd(p-t-Bu$_3$)$_2$) (170 mg, 0.34 mmol) was added thereto, and then refluxed for 48 hours. After cooling to normal temperature, purification was performed by the column chromatography. After drying, Formula 1-1 (6 g, 31%) was obtained.

MS: [M+H]$^+$=580

<Synthesis Example 2> Manufacturing of the Compound Represented by Formula 1-2

(1) Manufacturing of Formula 1A 2-bromodibenzothiophene (30 g, 114 mmol), 4-chlorophenylboronic acid (19.6 g, 125 mmol), and potassium carbonate (K$_2$CO$_3$) (39.4 g, 285 mmol) were dissolved in tetrahydrofuran (THF) (300 mL) and H$_2$O (100 ml) and heated to 50° C. Tetrakis(triphenylphosphine) palladium

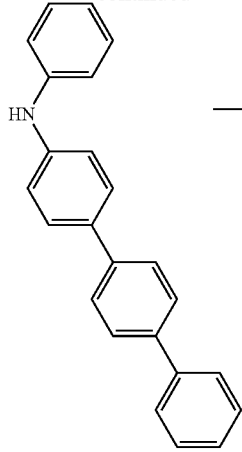

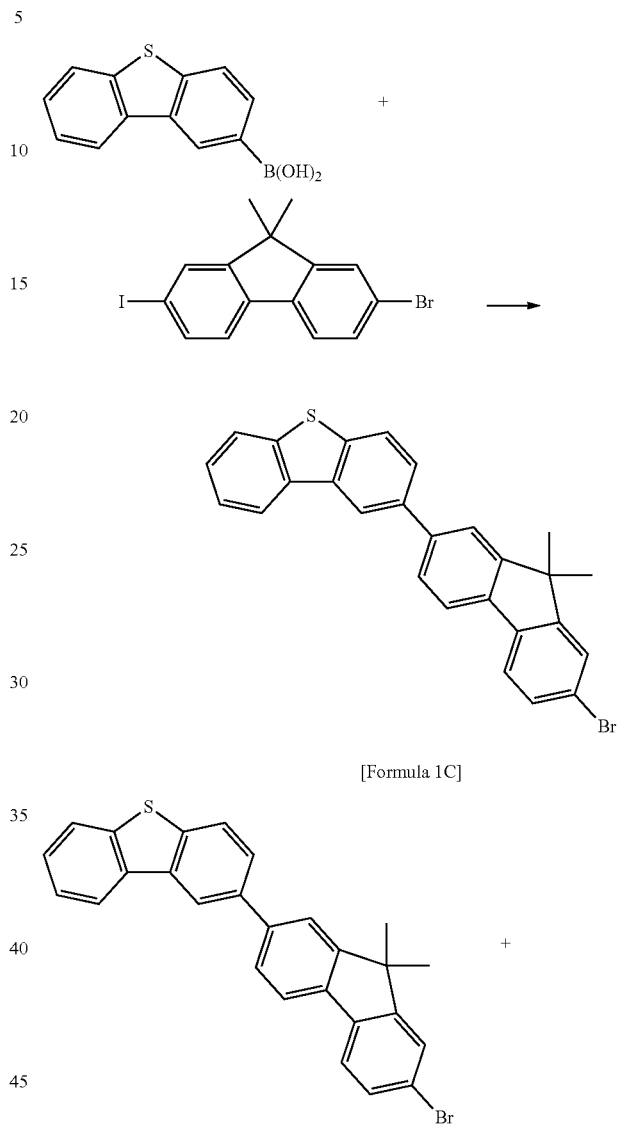

<Synthesis Example 3> Manufacturing of the Compound Represented by Formula 1-3

[Formula 1C]

[Formula 1C]

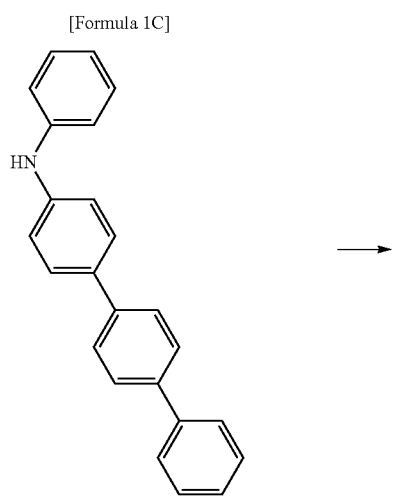

(1) Manufacturing of Formula 1B

The same method as the manufacturing of compound 1A of Synthesis Example 1 was performed to obtain Formula 1B (25 g, yield 59%), except that compound 4-chlorobiphenylboronic acid (25 g, 125 mmol) was used instead of compound 4-chlorophenylboronic acid.

MS: [M+H]$^+$=371

(2) Manufacturing of Formula 1-2

Formula 1B (10 g, 27 mmol), phenyl-terphenylamine (N-phenyl-[1,1':4',1''-terphenyl]-4-amine) (9.1 g, 28.4 mmol), NaOtBu (3.4 g, 35.1 mmol), and xylene (100 ml) were mixed, and then heated to 100° C. Bis[(tri-tertiary-butyl)phosphine]palladium (Pd(p-t-Bu$_3$)$_2$) (138 mg, 0.27 mmol) was added thereto, and then refluxed for 48 hours. After cooling to normal temperature, purification was performed by the column chromatography. After drying, Formula 1-2 (7.3 g, 41%) was obtained.

MS: [M+H]$^+$=656

-continued

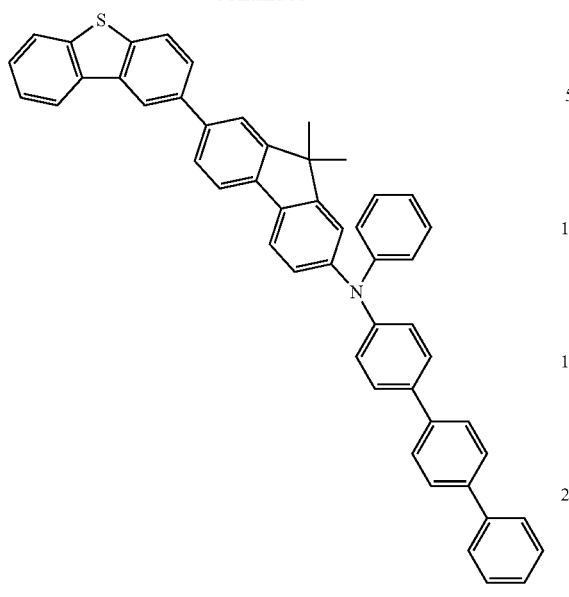

[Formula 1-3]

(1) Manufacturing of Formula 1C 2-dibenzothiopheneboronic acid (10 g, 43.9 mmol), 2-bromo-7-iodo-9,9-dimethyl-9H-fluorene (17.5 g, 43.9 mmol), and potassium carbonate ($K_2CO_3$) (18.2 g, 132 mmol) were dissolved in tetrahydrofuran (THF) (300 mL) and 100 ml of $H_2O$ and heated to 50° C. Tetrakis(triphenylphosphine) palladium ($Pd(PPh_3)_4$) (1.0 g, 0.88 mmol) was added thereto, and then refluxed for 12 hours. After cooling to normal temperature, the water layer was removed. After magnesium sulfate ($MgSO_4$) was added to the organic layer, filtration was performed. After concentration, purification was performed by the column chromatography to obtain Formula 1C (15 g, yield 75%).

MS: $[M+H]^+=455$ (2) Manufacturing of Formula 1-3

The same method as the manufacturing of compound 1-1 of Synthesis Example 1 was performed to obtain compound 1-3 (7 g, 46%), except that compound 1C (10 g, 22 mmol) was used instead of compound 1A.

MS: $[M+H]^+=695$

<Synthesis Example 4> Manufacturing of the Compound Represented by Formula 1-4

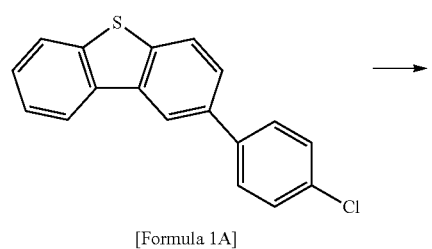

[Formula 1A]

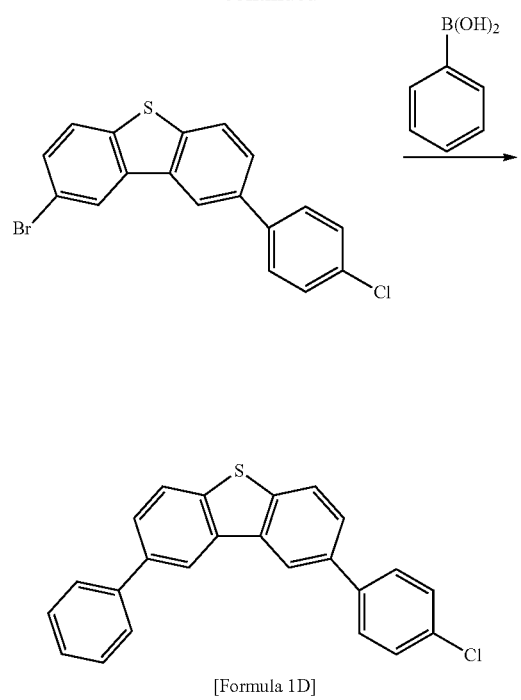

[Formula 1D]

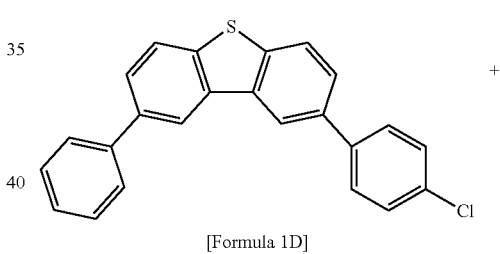

[Formula 1D]

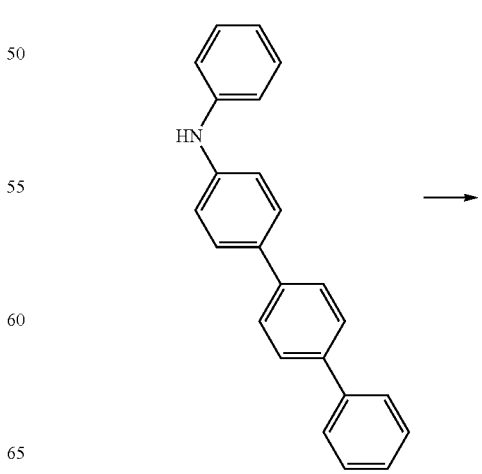

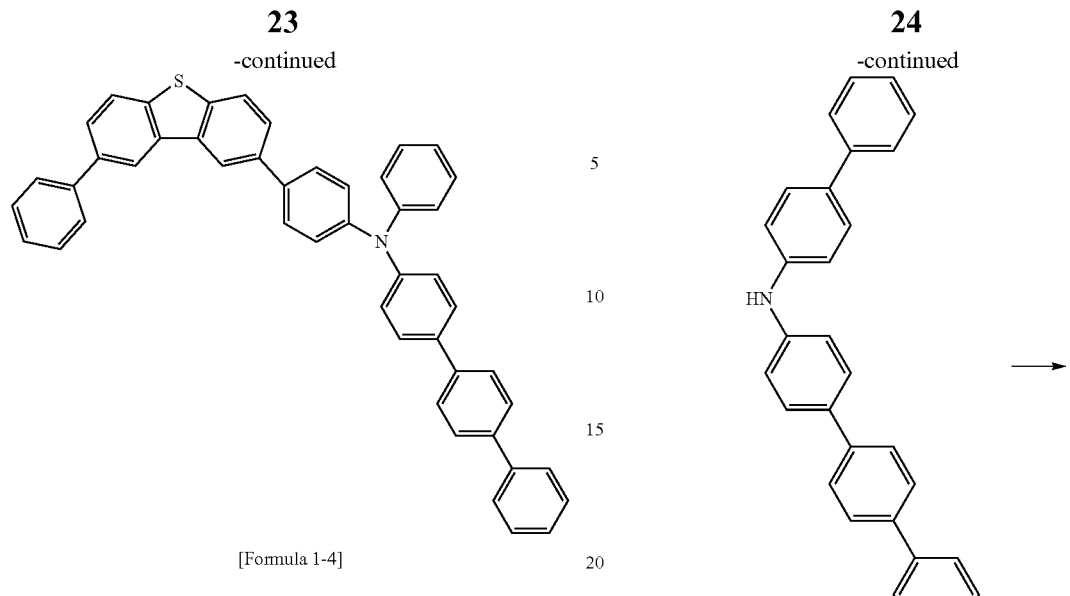

[Formula 1-4]

(1) Manufacturing of Formula 1D

After compound 1A (30 g, 102 mmol) was added to the flask including 1 L of dichloromethane and then dissolved therein, the solution in which bromine (5.26 ml, 102 mmol) was diluted in 400 ml of dichloromethane was slowly added in drops to the flask and agitated for 12 hours. After the reaction was finished, the reaction solution included in the flask was washed with the sodium bicarbonate saturated aqueous solution, and the organic layer was separated from the flask, dried by anhydrous magnesium sulfate, and filtered. The filtrate solution was concentrated, and recrystallized by dichloromethane and ethanol to obtain the white solid compound (15.2 g, 40%).

This compound was dissolved together with the phenyl-boronic acid (5.5 g, 44.8 mmol) and potassium carbonate ($K_2CO_3$) (16.9 g, 122 mmol) in tetrahydrofuran (THF) (400 ml) and 150 ml of water, and heated to 90° C. Tetrakis(triphenylphosphine) palladium ($Pd(PPh_3)_4$) (0.94 g, 0.81 mmol) was added thereto, and then refluxed for 12 hours. After cooling to normal temperature, the water layer was removed. After magnesium sulfate ($MgSO_4$) was added to the organic layer, filtration was performed. After concentration, purification was performed by the column chromatography to obtain Formula 1D (8 g, yield 51%).

MS: $[M+H]^+=371$ (2) Manufacturing of Formula 1-4

The same method as the manufacturing of compound 1-1 of Synthesis Example 1 was performed to obtain compound 1-4 (9.75 g, 55%), except that compound 1D (10 g, 27 mmol) was used instead of compound 1A.

MS: $[M+H]^+=656$

<Synthesis Example 5> Manufacturing of the Compound Represented by Formula 1-7

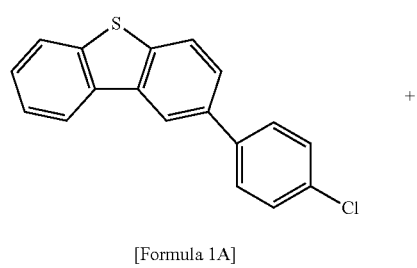

[Formula 1A]

+

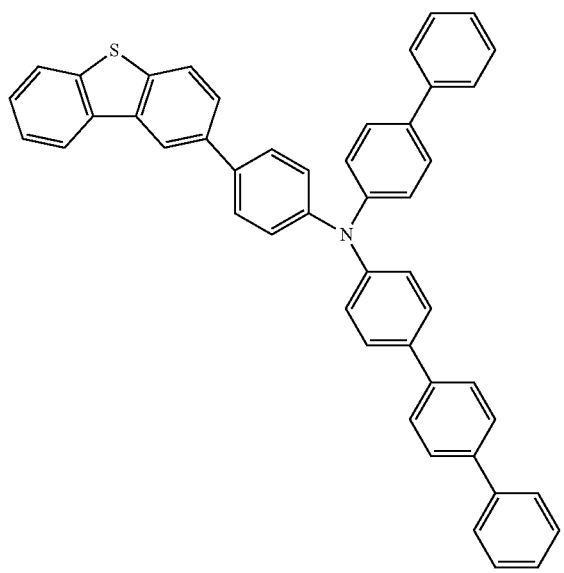

[Formula 1-7]

(1) Manufacturing of Formula 1-7

The same method as the manufacturing of compound 1-1 of Synthesis Example 1 was performed to obtain compound 1-7 (8.9 g, 40%), except that compound biphenyl-terphenylamine (N-biphenyl-[1,1':4',1"-terphenyl]-4-amine) (14.1 g, 35.6 mmol) was used instead of compound phenyl-terphenylamine (N-phenyl-[1,1':4',1"-terphenyl]-4-amine).

MS: $[M+H]^+=656$

<Synthesis Example 6> Manufacturing of the Compound Represented by Formula 1-8

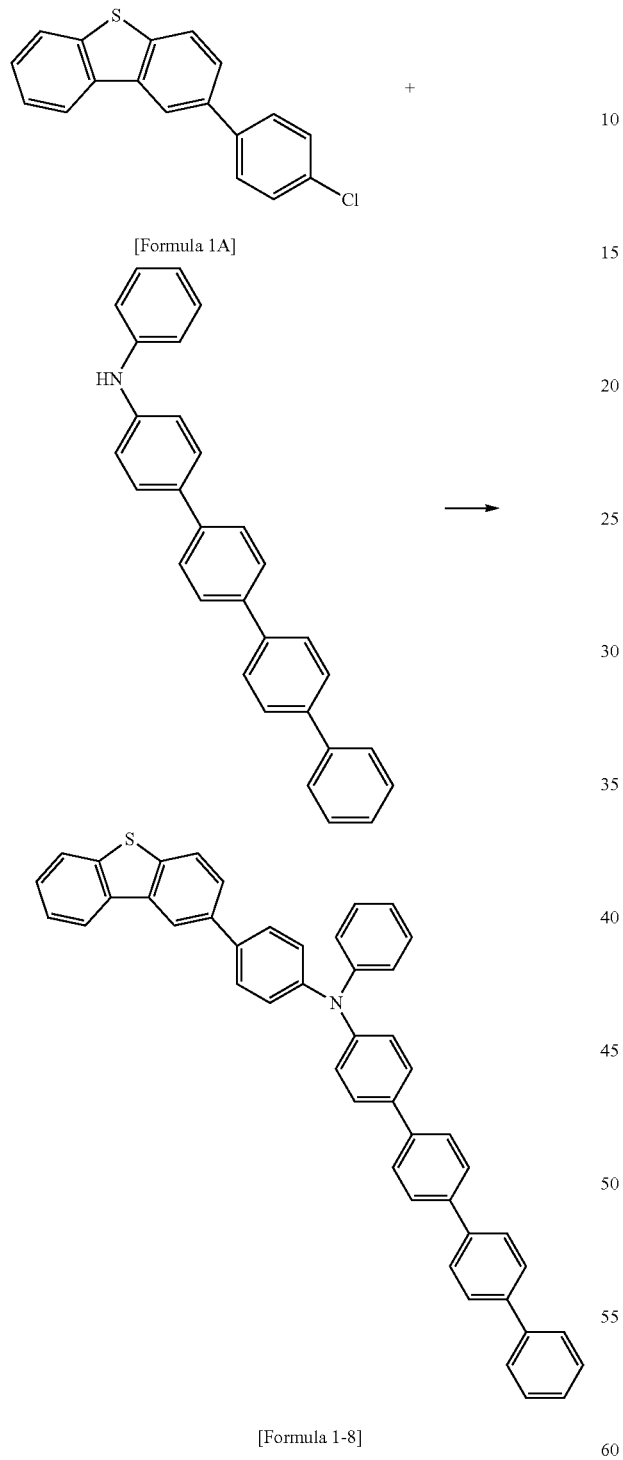

[Formula 1A]

[Formula 1-8]

(1) Manufacturing of Formula 1-8

The same method as the manufacturing of compound 1-1 of Synthesis Example 1 was performed to obtain compound 1-8 (10 g, 45%), except that compound phenyl-tetraphenylamine (N-phenyl-[1,1':4',1''-tetraphenyl]-4-amine) (14.1 g, 35.6 mmol) was used instead of compound phenyl-terphenylamine (N-phenyl-[1,1':4',1''-terphenyl]-4-amine).

MS: $[M+H]^+=656$

Example 1

A glass substrate (Corning 7059 glass) on which a thin film of ITO (indium tin oxide) was applied to a thickness of 1000 Å was added to distilled water having a dispersing agent dissolved therein, and washed with ultrasonic waves. The detergent as used herein was a product commercially available from Fisher Co., and distilled water was one which had been twice filtered by using a filter commercially available from Millipore Co. ITO was washed for 30 minutes, and washing with ultrasonic waves was then repeated twice for 10 minutes by using distilled water. After the completion of washing with distilled water, washing with ultrasonic waves was performed by using isopropyl alcohol, acetone, and methanol solvents in the order, and drying was performed.

Hexanitrile hexaazatriphenylene was vacuum deposited by heat to thicknesses of 500 Å to form a hole injection layer on the prepared ITO transparent electrode. After Formula 1-1 (400 Å) that was the material transporting the holes and synthesized in the Synthesis Example 1 was vacuum deposited thereon, the host H1 and the dopant D1 compound were vacuum deposited in a thickness of 300 Å as a light emitting layer. Thereafter, the E1 compounds (300 Å) were sequentially vacuum deposited by heat as electron injection and transport layers. Lithium fluoride (LiF) in a thickness of 12 Å and aluminum in a thickness of 2000 Å were subsequently deposited on the electron transport layer to form a cathode, thereby manufacturing the organic light emitting device.

In the aforementioned process, the deposition speed of the organic material was maintained at 1 Å/sec, that of lithium fluoride was maintained at 0.2 Å/sec, and that of aluminum was maintained at 3 to 7 Å/sec.

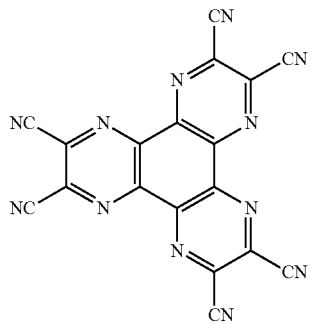

[hexanitrile hexaazatriphenylene]

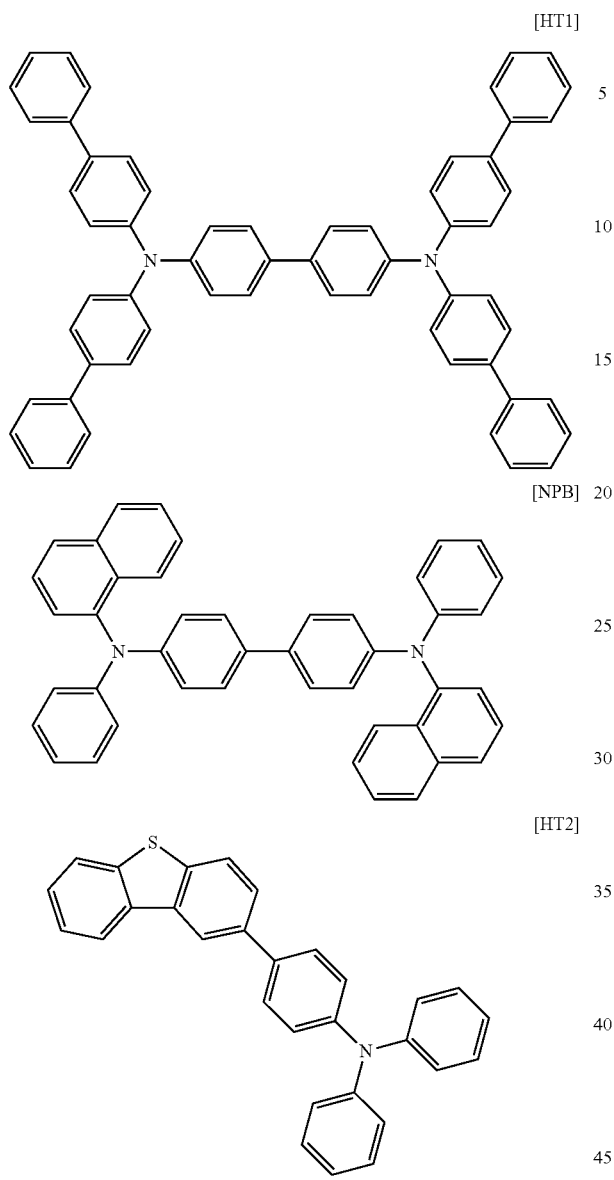

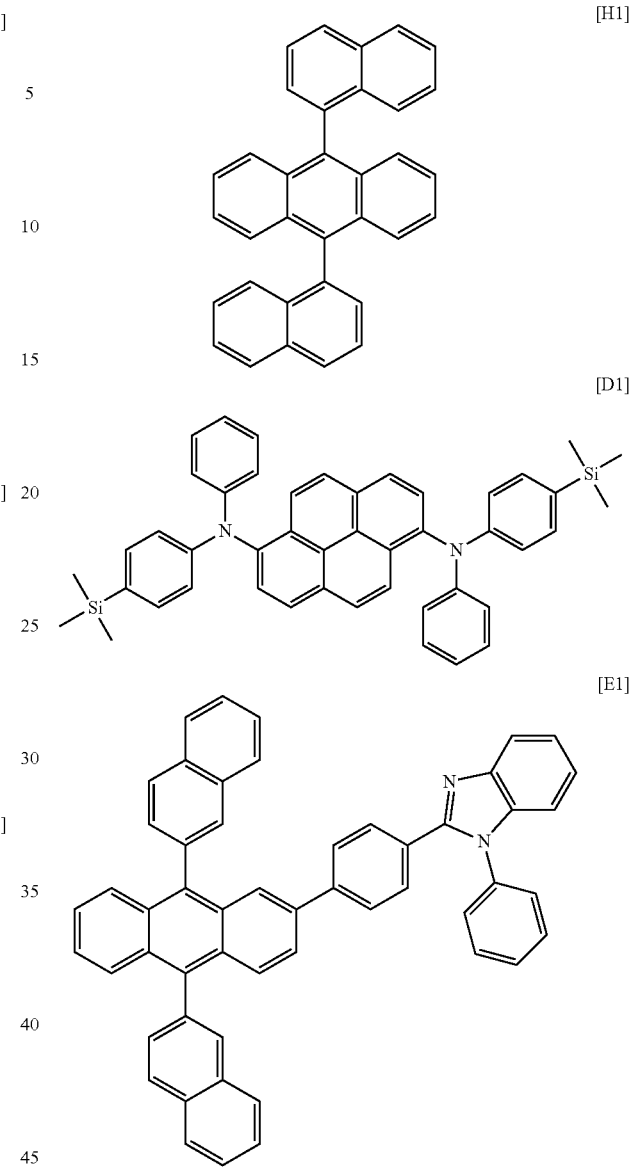

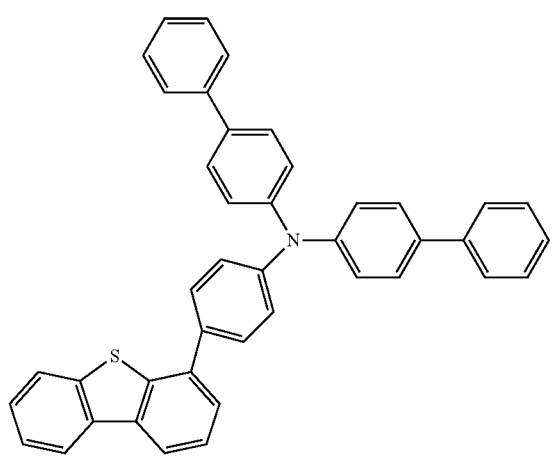

Example 2

The same experiment as Example 1 was performed, except that Formula 1-2 was used instead of Formula 1-1 synthesized in Synthesis Example 1 as the hole transport layer.

Example 3

The same experiment as Example 1 was performed, except that Formula 1-3 was used instead of Formula 1-1 synthesized in Synthesis Example 1 as the hole transport layer.

Example 4

The same experiment as Example 1 was performed, except that Formula 1-5 was used instead of Formula 1-1 synthesized in Synthesis Example 1 as the hole transport layer.

Example 5

The same experiment as Example 1 was performed, except that Formula 1-7 was used instead of Formula 1-1 synthesized in Synthesis Example 1 as the hole transport layer.

Example 6

The same experiment as Example 1 was performed, except that Formula 1-8 was used instead of Formula 1-1 synthesized in Synthesis Example 1 as the hole transport layer.

Comparative Example 1

The same experiment as Example 1 was performed, except that HT1 was used instead of Formula 1-1 synthesized in the Synthesis Example as the hole transport layer.

Comparative Example 2

The same experiment as Example 1 was performed, except that NPB was used instead of Formula 1-1 synthesized in the Synthesis Example as the hole transport layer.

Comparative Example 3

The same experiment as Example 1 was performed, except that HT2 was used instead of Formula 1-1 synthesized in the Synthesis Example as the hole transport layer.

Comparative Example 4

The same experiment as Example 1 was performed, except that HT3 was used instead of Formula 1-1 synthesized in the Synthesis Example as the hole transport layer.

Like Examples 1 to 6 and Comparative Examples 1 to 4, the test results of the organic light emitting device manufactured by using each compound as the hole transport layer material are described in Table 1.

TABLE 1

| Experimental Example 50 mA/cm$^2$ | HTL material | Voltage (V) | Current efficiency (cd/A) |
| --- | --- | --- | --- |
| Comparative Example 1 | HT1 | 6.25 | 5.98 |
| Comparative Example 2 | NPB | 6.21 | 5.87 |
| Comparative Example 3 | HT2 | 6.42 | 6.07 |
| Comparative Example 4 | HT3 | 7.11 | 6.53 |
| Example 1 | Formula 1-1 | 6.02 | 7.02 |
| Example 2 | Formula 1-2 | 6.10 | 7.05 |
| Example 3 | Formula 1-3 | 6.01 | 7.05 |
| Example 4 | Formula 1-5 | 6.04 | 7.02 |
| Example 5 | Formula 1-7 | 6.05 | 7.06 |
| Example 6 | Formula 1-8 | 6.02 | 7.01 |

As seen in Table 1, in the case of the organic light emitting device manufactured by using the compound of the present specification as the hole transport layer material, efficiency, driving voltage, and stability are excellent as compared to the case where a known material is used.

Further, as seen in Table 1, in the case of the organic light emitting device manufactured by using the compound of the present specification as the hole transport layer material, hole injection efficiency into the light emitting layer may be increased, such that a low voltage is feasible and efficiency is excellent as compared to the case where $R_2$ and $R_3$ are the same.

Further, as seen in Table 1, in the case of the organic light emitting device manufactured by using the compound of the present specification as the hole transport layer material, an electron donating effect of S to the connected amine group may be ensured to increase injection and transporting efficiencies of the holes to the light emitting layer, thus, the voltage and efficiency are excellent as compared to the case of Comparative Example 4 in which amine is substituted to a 13$^{th}$ position of dibenzothiophene.

The invention claimed is:

1. A dibenzothiophene-based compound represented by the following Formula 1:

[Formula 1]

wherein, $L_1$ is an arylene group having 6 to 40 carbon atoms; or a fluorenylene group substituted by an alkyl group, $R_1$ is hydrogen; an alkyl group having 1 to 20 carbon atoms; an alkoxy group having 1 to 20 carbon atoms; or an aryl group having 6 to 12 carbon atoms substituted or unsubstituted by an alkyl group having 1 to 20 carbon atoms or an alkoxy group having 1 to 20 carbon atoms, $R_2$ and $R_3$ are different from each other, $R_2$ is a phenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; or a biphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group, $R_3$ is a p-terphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; a p-tetraphenyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group; or a naphthyl group substituted or unsubstituted by one or more substituent groups selected from the group consisting of an alkyl group having 1 to 20 carbon atoms, an alkenyl group having 2 to 20 carbon atoms, an alkoxy group having 1 to 20 carbon atoms, a fluorenyl group, a nitrile group, and a nitro group, $R_4$ is hydrogen; an alkyl group having 1 to 20 carbon atoms, or an alkoxy group having 1 to 20 carbon atoms, and may form an aliphatic, aromatic, or hetero condensated cycle with an adjacent group, and n means the number of substituent groups, and is an integer of 1 to 6.

2. The dibenzothiophene-based compound of claim 1, wherein $R_1$ is hydrogen; or a phenyl group substituted or unsubstituted by an alkyl group having 1 to 20 carbon atoms.

3. The dibenzothiophene-based compound of claim 1, wherein $R_2$ is a phenyl group; or a biphenyl group.

4. The dibenzothiophene-based compound of claim 1, wherein $R_3$ is a p terphenyl group or a p tetraphenyl group.

5. The dibenzothiophene-based compound of claim 1, wherein $L_1$ is a phenylene group, a biphenylene group, or a fluorenylene group substituted by an alkyl group.

6. The dibenzothiophene-based compound of claim 1, wherein $R_2$ and $R_3$ are different from each other, $R_2$ is a phenyl group, and $R_3$ is a p terphenyl group.

7. The dibenzothiophene-based compound of claim 1, wherein $R_2$ and $R_3$ are different from each other, $R_2$ is a biphenyl group, and $R_3$ is a p terphenyl group.

8. The dibenzothiophene-based compound of claim 1, wherein $R_2$ and $R_3$ are different from each other, $R_2$ is a phenyl group, and $R_3$ is a p tetraphenyl group.

9. The dibenzothiophene-based compound of claim 1, wherein $R_2$ and $R_3$ are different from each other, $R_2$ is a biphenyl group, and $R_3$ is a p tetraphenyl group.

10. The dibenzothiophene-based compound of claim 1, wherein $L_1$ is a phenylene group, a biphenylene group, or a fluorenylene group substituted by an alkyl group, $R_1$ is hydrogen, or a phenyl group substituted or unsubstituted by an alkyl group having 1 to 20 carbon atoms, $R_2$ and $R_3$ are different from each other, $R_2$ is a phenyl group or a biphenyl group, and $R_3$ is a p terphenyl group or a p tetraphenyl group.

11. The dibenzothiophene-based compound of claim 1, wherein Formula 1 is any one of the following Formulas 1-1 to 1-8

[Formula 1-1]

[Formula 1-2]

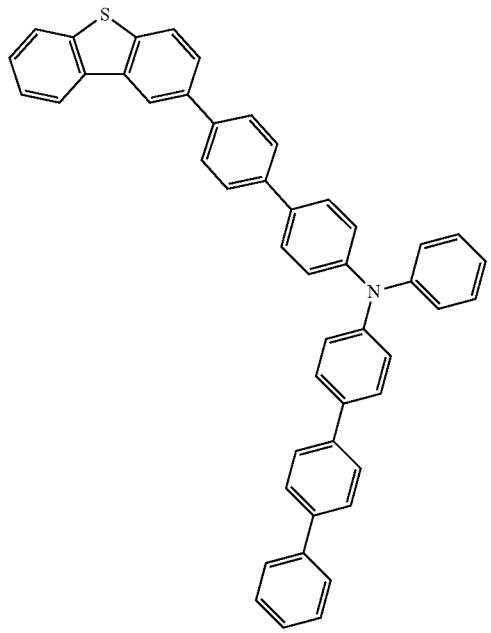

[Formula 1-3]

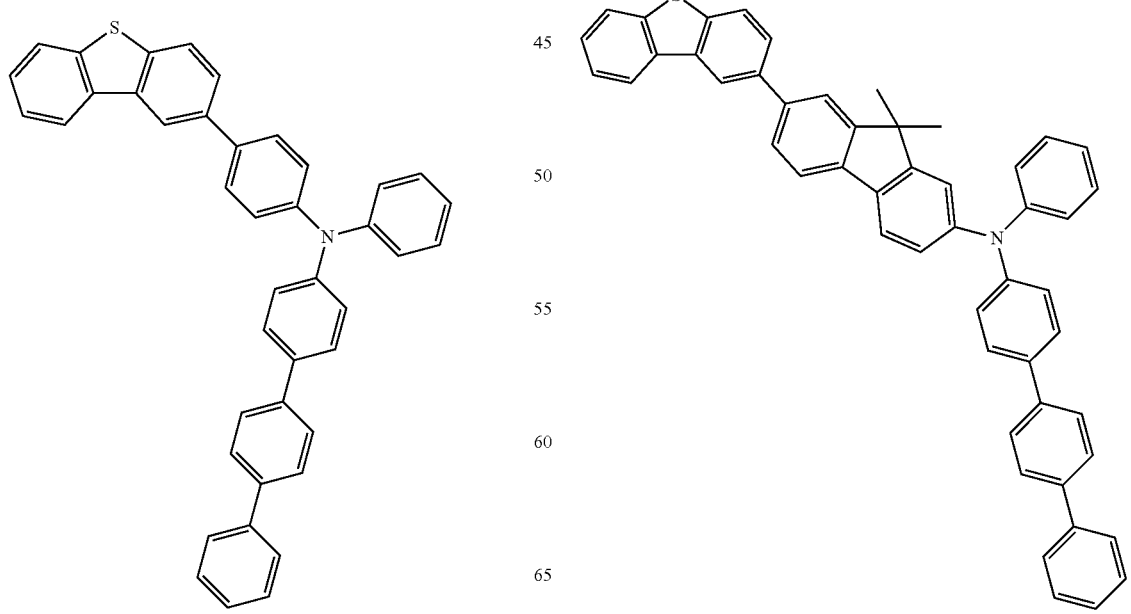

[Formula 1-4]
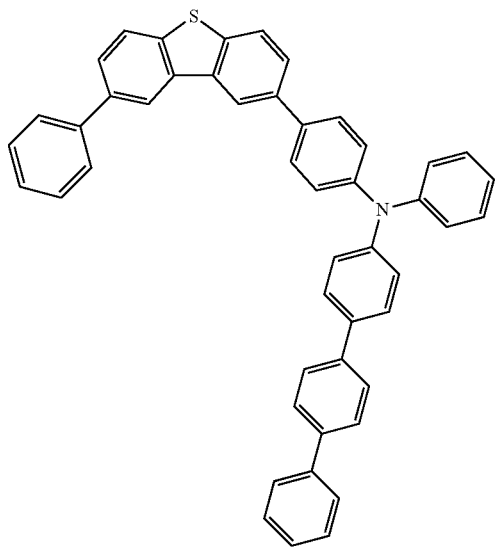
[Formula 1-5]
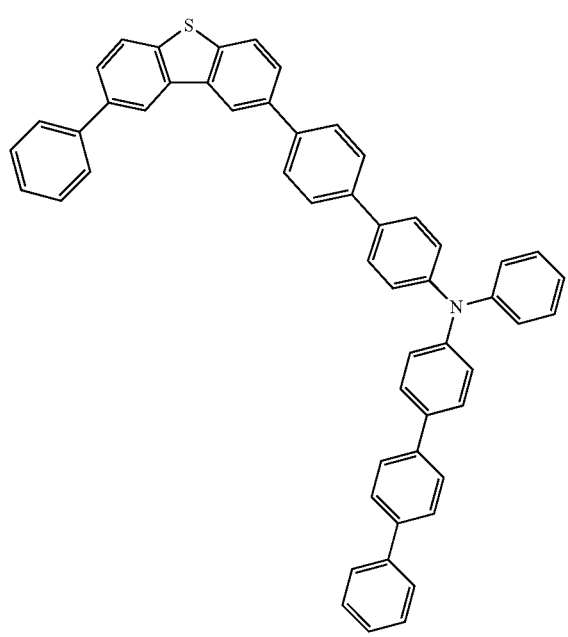
[Formula 1-6]
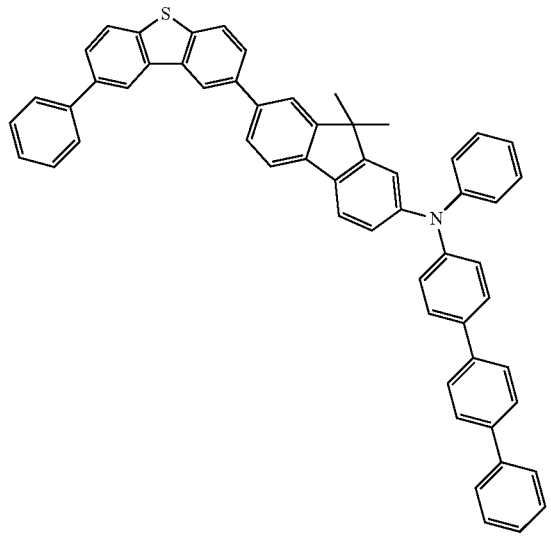
[Formula 1-7]
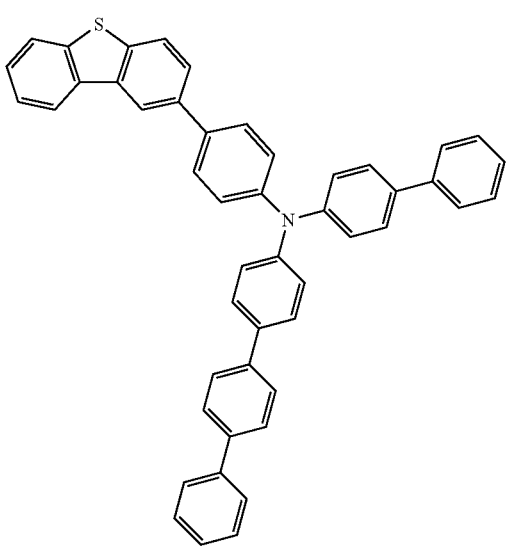

-continued

[Formula 1-8]

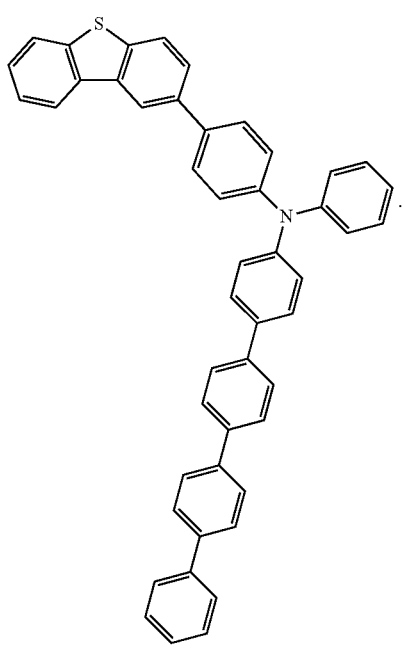

12. An organic light emitting device comprising:
a first electrode,
a second electrode, and
organic material layers formed of one or more layers comprising a light emitting layer disposed between the first electrode and the second electrode,
wherein one or more layers of the organic material layers comprise the dibenzothiophene-based compound according to claim 1, or a compound in which a heat curable or photocurable functional group is introduced into the dibenzothiophene based compound.

13. The organic light emitting device of claim 12, wherein the organic material layers comprise a hole transport layer, and the hole transport layer comprises the dibenzothiophene-based compound.

14. The organic light emitting device of claim 12, wherein the organic material layers comprise a first hole transport layer and a second hole transport layer, the first hole transport layer comprises the dibenzothiophene-based compound and the second hole transport layer comprises an aromatic amine compound.

15. The organic light emitting device of claim 14, wherein the first hole transport layer is interposed between the light emitting layer and the second hole transport layer.

16. The organic light emitting device of claim 14, wherein the first hole transport layer is in contact with the light emitting layer.

17. The organic light emitting device of claim 12, wherein the organic material layers comprise a hole injection layer, or a layer simultaneously injecting and transporting holes and the hole injection layer and the layer simultaneously injecting and transporting holes comprises the dibenzothiophene-based compound.

18. The organic light emitting device of claim 12, wherein the organic material layers comprise an electron injection and electron transport layer, and the electron injection or electron transport layer comprises the dibenzothiophene-based compound.

19. The organic light emitting device of claim 12, wherein the organic material layers comprise the light emitting layer, and the light emitting layer comprises the dibenzothiophene-based compound, or the compound in which the heat curable or photocurable functional group is introduced into the dibenzothiophene based compound.

* * * * *